United States Patent [19]

Weingarten

[11] 4,425,428
[45] Jan. 10, 1984

[54] NOVEL PEPTIDE AND PEPTOLIDE SUBSTRATES FOR MAMMALIAN COLLAGENASE

[75] Inventor: Harold I. Weingarten, University City, Mo.

[73] Assignee: Monsanto Company, St. Louis, Mo.

[21] Appl. No.: 485,762

[22] Filed: Apr. 18, 1983

Related U.S. Application Data

[62] Division of Ser. No. 366,520, Apr. 8, 1982.

[51] Int. Cl.³ .................... C12Q 1/38; C12Q 1/36; C07C 103/52
[52] U.S. Cl. ............................ 435/23; 435/4; 435/13; 435/24; 260/112.5 R
[58] Field of Search ............ 260/112.5 R; 435/23, 435/24, 4, 13

[56] References Cited

U.S. PATENT DOCUMENTS

4,138,394  2/1979  Sakabara et al. ............ 260/112.5 R
4,176,009  11/1979 Sakabara et al. ..................... 435/24

OTHER PUBLICATIONS

Nagai et al., *Biochimica, Biophysica Acta* vol. 445, pp. 521–524 (1976).
Masui et al., *Biochem. Med.* vol. 17, pp. 215–221 (1977).

*Primary Examiner*—Thomas G. Wiseman
*Assistant Examiner*—Frederick W. Pepper
*Attorney, Agent, or Firm*—Scott J. Meyer; James W. Williams, Jr.

[57] ABSTRACT

Method for determination of the enzyme collagenase by reacting the enzyme with a peptide or peptolide substrate having the following amino acid sequences:

$R_1$-Pro-Leu-Gly-Ile-Leu-Gly-Leu-$R_2$,
$R_1$-Gly-Pro-Leu-Gly-Ile-Leu-Gly-Ala-$R_2$,
$R_1$-Pro-Leu-Gly(O-Ile)-Leu-$R_2$,
$R_1$-Pro-Leu-Gly(O-Leu)-Leu-$R_2$, and
$R_1$-Pro-Leu-Gly(O-Leu)-Ala-$R_2$, wherein $R_1$ is H or N-protecting group, and $R_2$ is terminal amide, carboxyl or ester group.

3 Claims, No Drawings

NOVEL PEPTIDE AND PEPTOLIDE SUBSTRATES FOR MAMMALIAN COLLAGENASE

This is a division of application Ser. No. 366,520, filed Apr. 8, 1982.

BACKGROUND OF THE INVENTION

This invention relates to novel peptides and peptolides which have high activity as substrates for mammalian collagenase.

Collagenase is a proteolytic enzyme which acts on the protein collagen. This enzyme was early found in certain clostridia culture filtrates and shown to act specifically on native (undenatured) collagen at near physiological pH. See Mandl, "Collagenase and Elastases," *Advances in Enzymology* 23, p. 163, Interscience Publishers, New York, 1961. An illustrative example of a collagenase enzyme product obtained from special strains of *Clostridium histolyticum* is commercially available from Worthington Biochemical Corporation, Freehold, N.J.

Collagenolytic enzymes also have been obtained by tissue and cell culture from a wide range of mammalian species in which collagen is metabolized under both physiological and pathological conditions. Collagenase enzymes from such cell and tissue culture sources or from tissue extracts are usually obtained in exceedingly small amounts. Consequently, such enzymes are usually available only by laboratory preparation. An illustrative example of such a preparation is a purified collagenase obtained from culture media of tadpole explant as described by Nagai et al., *Biochim. Biophys. Acta* 263, 564–573 (1972).

The natural substrate collagen constitutes the connective tissue of the body and is the major type of fibrous protein in higher vertebrae, including mammals. In man, approximately one-third of the total protein content is collagen. The ability of collagenase to digest native collagen provides the enzyme with a variety of uses in tissue culture and cell studies including the isolation of tissue collagen and other types of tissue dissociation. Illustratively, achilles-tendon collagen is hydrolyzed by collagenase to peptides with an average chain length of four to five amino acids.

Collagenase also is believed to be associated with the tissue invasion process in tumor angiogenesis, in arthritic conditions such as rheumatoid arthritis, in corneal ulceration and other diseases of connective tissue. It has been suggested that tumor angiogenesis factor (TAF) induces collagenase secretion by blood vessel endothelial cells. See Moscatelli et al., *Cell* 20, 343 (1980). The ability of TAF to stimulate collagenase production in endothelial cells provides a basis for assay for TAF and anti-TAF. Accordingly, the measurement of collagenase production is a useful diagnostic tool for tissue invasion.

Conventional assays for collagenase generally are based on methodology developed by Mandl et al., *J. Clin. Invest.* 32, 1323 (1953). According to these assay procedures, collagenase is incubated for an extended period of time at 37° C. with native collagen. The extent of collagen breakdown is then determined using the Moore and Stein colorimetric ninhydrin method, *J. Biol. Chem.* 176, 367 (1948). Amino acids which are liberated are expressed as micromoles per milligram of collagenase. One unit of enzyme activity equals the amount of collagenase required to solubilize one micromole of leucine equivalents.

Various synthetic substrates also have been developed heretofore as reagents for the quantitative determination of proteolytic enzymes such as thrombin, plasmin, trypsin and collagenase. These substrates generally consist of relatively short chain peptides. Under the action of the appropriate enzyme, a fragment is hydrolytically split off from the substrate with the resulting formation of a split product, the quantity of which can be measured by conventional photometric, spectrophotometric, fluorescence-photometric, and chromatographic methods. The quantity of the split product formed per time unit is a measure for the enzyme activity from which the quantity of enzyme present in a given test sample can be calculated.

The following are examples of two such synthetic collagenase substrates which are commercially available from Penninsula Labs, San Carlos, Calif.:
DNP-Pro-Leu-Gly-Ile-Ala-Gly-Arg-$NH_2$ and
DNP-Pro-Gln-Gly-Ile-Ala-Gly-Gln-D-Arg-OH,
wherein DNP=Dinitrophenyl.

Other examples of peptide substrates for mammalian collagenase and methods of measuring collagenase activity with the substrates are described in U.S. Pat. Nos. 4,138,394 and 4,176,009; Nagai et al., *Biochim. Biophys. Acta* 445, 521–524 (1976); and Masui et al., *Biochem. Med.* 17, 215–221 (1977). Further background information on mammalian collagenase also can be had by reference to the treatise "Collagenase in Normal and Pathological Connective Tissues," Woolley and Evanson, Eds., John Wiley & Son, New York, 1980.

DESCRIPTION OF THE INVENTION

In accordance with the present invention a series of novel peptides and peptolides have been synthesized as substrates for the enzyme collagenase. They have been found to have substantially greater activity than the aforesaid commercially available synthetic substrates for mammalian collagenase. The novel peptide and peptolides of this invention are selected from the group consisting of:

Peptides
$R_1$-Pro-Leu-Gly-Ile-Leu-Gly-Leu-$R_2$,
$R_1$-Gly-Pro-Leu-Gly-Ile-Leu-Gly-Ala-$R_2$,
Peptolides
$R_1$-Pro-Leu-Gly(O-Ile)-Leu-$R_2$,
$R_1$-Pro-Leu-Gly(O-Leu)-Leu-$R_2$, and
$R_1$-Pro-Leu-Gly(O-Leu)-Ala-$R_2$,
wherein
  $R_1$=H or N-protecting group, and
  $R_2$=terminal amide, carboxyl or ester group.

The abbreviations used for the amino acids herein follow standard nomenclature in which:
Ala=L-alanine,
Gly=L-glycine,
Ile=L-isoleucine,
Leu=L-leucine, and
Pro=L-proline.

The novel peptides of this invention can be made by appropriate adaptation of conventional methods for peptide synthesis. Thus, the peptide chain can be prepared by a series of coupling reactions in which the constituent amino acids are added to the growing peptide chain in the desired sequence. The use of various N-protecting groups, e.g., the carbobenzoxy group or the t-butyloxycarbonyl group (BOC), various coupling reagents, e.g., dicyclohexylcarbodiimide, carbonyldiimidazole, or 1-hydroxybenzotriazole monohydrate (HBT), and various cleavage reagents, e.g., trifluoracetic acid, HCL in dioxane, boron tris(trifluoroacetate) and cyanogen bromide, and reaction in solution with isolation and purification of intermediates is well-known classical peptide methodology.

Preferably, the peptides of this invention are prepared by the well-known Merrifield solid support method. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxyl terminus to a solid support, usually cross-linked polystyrene or styrene-divinylbenzene copolymer. This method conveniently simplifies the number of procedural manipulations since removal of the excess reagents at each step is effected simply by washing of the polymer.

The general reaction sequence for the Merrifield peptide synthesis can be illustrated as follows:

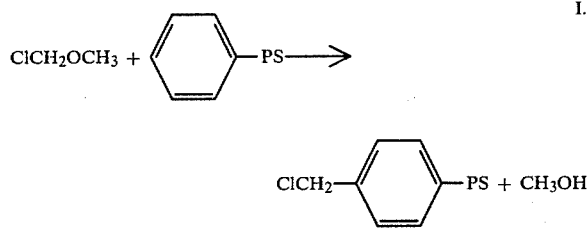

I.

Chloromethylation Step to provide reactive group for attachment of peptide, wherein PS=Polystyrene Residue.

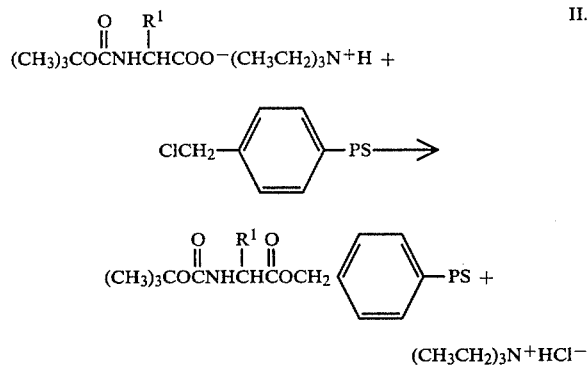

II.

Esterification Step—Reaction with Triethylammonium salt of the First Protected Amino Acid ($R^1$) Using t-BOC Protecting Group.

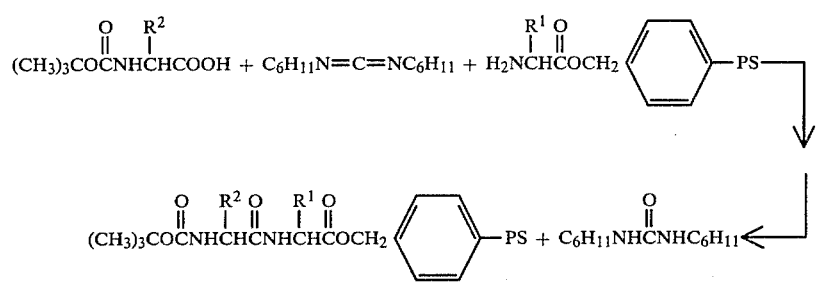

III.

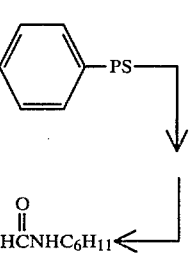

Peptide forming step with Dicyclohexylcarbodiimide Coupling Agent.

This step follows cleavage of t-BOC by HCl and liberation of N-terminal amine by excess of triethylamine, thereby enabling it to react with the activated carboxyl of the next protected amino acid ($R^2$). A final step involves cleavage of the completed peptide from the PS resin such as by anhydrous HBr in acetic acid or trifluoroacetic acid.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969.

The novel peptolides of this invention have been prepared by the following general synthetic scheme:

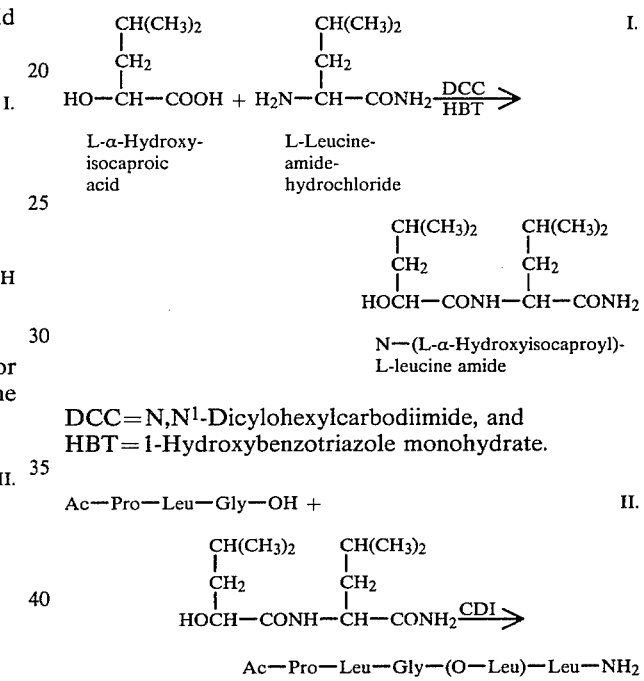

DCC=N,N¹-Dicylohexylcarbodiimide, and
HBT=1-Hydroxybenzotriazole monohydrate.

CDI=1,1'-Carbonyldiimidazole.

L-alanine amide hydrochloride can replace an equivalent amount of L-leucine amide hydrochloride, or L-isoleucic acid can replace an equivalent amount of L-α-hydroxyisocaproic acid, in reaction I above to respectively prepare the other two peptolides of the present invention.

In order to determine the activity of the novel peptide and peptolide substrates of the present invention, a standard collagenase enzyme solution was used to cleave the respective substrates, and the split products were then assayed by High Pressure Liquid Chromatography (HPLC). From their relative cleavage rates, the novel substrates were calculated to be from six to fifty times as active as the aforesaid commercially available collagenase substrates.

The following specific examples will further illustrate the invention although it should be understood that the invention is not limited to these specific examples.

EXAMPLE 1

KF Method of Amino Acid Attachment to Resin:*
Attachment of N-t-BOC-Glycine to Resin A mixture of (5.5 g, 0.031 mole) N-t-BOC-glycine, (3.6 g, 0.062 mole) potassium fluoride and (20 g, 0.0208 mole) Merrifield resin (1% crosslinked polystyrene; 200–400 mesh, 1 m.eq. chloride/gram) was suspended in 100 ml dimethylformamide (DMF) and stirred at 50° for 24 hrs. The resin was collected on a coarse fritted disk, washed twice with (DMF), 50% DMF in water, 50% ethanol in water and ethanol. The washed resin was then dried to a constant weight in vacuo, yielding 25.4 g of N-t-BOC-glycine on resin which gave a negative ninhydrin test and an amino acid analysis showing 0.714 m.mole/g attachment.

*See Horiki et al., Chem. Letters 165-168 (1978) for background information on this general method.

Substantially similar procedures were used to attach other amino acids to the resin by substituting equivalent amounts of the appropriate N-t-BOC- protected amino acid for N-t-BOC-glycine in the above procedure. The amino acids were selected such as to prepare the following peptide sequences:

A. Ac-Pro-Leu-Gly-Ile-Leu-Gly-Leu-OH,
and
B. Ac-Gly-Pro-Leu-Gly-Ile-Leu-Gly-Ala-OH
wherein Ac=acetyl.

In each case, dicyclohexylcarbodiimide (DCC) was used as the coupling agent in methylene chloride solvent. After initial coupling, the α-amino protecting group was removed by trifluoroacetic acid (TFA) in methylene chloride solvent followed by triethylamine (TEA) in methylene chloride. After removal of the α-amino protecting group, the remaining protected amino acids were coupled stepwise in the aforesaid order to obtain the desired peptide sequence. Each protected amino acid was reacted in excess DCC in methylene chloride solvent. After the amino acid sequence was completed, the peptide was removed from the resin support by treatment with anhydrous HF. At each step, excess reagents were removed by washing the resin with methanol and/or methylene chloride solvents.

The sequence of reaction and washing steps carried out for each amino acid addition to the growing peptide chain for preparation of the aforesaid peptides by the solid state peptide synthesis is set forth in the following Table 1.

TABLE 1

Protocol Used for Solid-State Peptide Synthesis

| Wash or Reactant | Shake Duration |
|---|---|
| 1. Methylene chloride | 1 min. |
| 2. 50% TFA/methylene chloride | 1 min. |
| 3. 50% TFA/methylene chloride | 20 min. |
| 4. Methylene chloride | 1 min. |
| 5. Methylene chloride | 1 min. |
| 6. Methylene chloride | 1 min. |
| 7. 10% TEA/methylene chloride | 1 min. |
| 8. Methanol | 1 min. |
| 9. 10% TEA/methylene chloride | 1 min. |
| 10. Methylene chloride | 1 min. |
| 11. Methanol | 1 min. |
| 12. Methylene chloride | 1 min. |
| 13. Amino acid/methylene chloride | 1 min. |
| 14. DCC/methylene chloride | 30–90 min. |
| 15. Methylene chloride | 1 min. |
| 16. Methanol | 1 min. |
| 17. Methylene chloride | 1 min. |
| 18. Methanol | 1 min. |
| | 66–126 min. (1–2 hrs.) |

At step 14 the progress of the coupling is monitored by a ninhydrin color test.

A

Synthesis of Ac-Pro-Leu-Gly-Ile-Leu-Gly-Leu-OH

To a 5 g sample of L-leucine on resin (0.57 μmole/mg attachment) was added (1.5 g, 8.6 mm) t-BOC-glycine in step 13 of the aforesaid protocol. This procedure was repeated with the appropriate t-BOC-protected amino acids to produce the peptide Ac-Pro-Leu-Gly-Ile-Leu-Gly-Leu-OH. The peptide was removed from the resin by anhydrous HF, extracted into methanol, and the methanol was then removed by evaporation. The one gram of crude peptide obtained was purified by recrystallization from methanol in water, m.p. 220° C.

Analysis: Calc'd. for $C_{35}H_{61}O_9N_7$: C, 58.1; H, 8.5; N, 13.5. Found: C, 57.8; H, 8.5; N, 13.4.

B

Synthesis of Ac-Gly-Pro-Leu-Gly-Ile-Leu-Gly-Ala-OH

To a 3 g sample of L-alanine on resin (0.57 μmole/mg attachment) was added (0.9 g, 5.16 mm) t-BOC-glycine in step 13 of the aforesaid protocol. This procedure was repeated with the appropriate t-BOC-protected amino acids to produce the peptide Ac-Gly-Pro-Leu-Gly-Ile-Leu-Gly-Ala-OH. The peptide was removed from the resin by anhydrous HF, extracted into methanol, and the methanol was then removed by evaporation; yielding one gram of crude peptide. A 200 mg sample was purified by the method described in Example 8, below, yielding 65 mg of purified product.

Analysis: Calc'd. for $C_{34}H_{58}O_{10}N_8 \cdot 3.5H_2O$: C, 51.0; H, 8.1; N, 14.0. Found: C, 51.2; H, 7.7; N, 13.6.

EXAMPLE 2

N-(L-α-Hydroxyisocaproyl)-L-Leucine Amide

To a solution of (4.6 g, 0.0275 mole) L-leucine amide hydrochloride and (3.3 g, 0.025 mole) L-α-hydroxyisocaproic acid in 150 ml dimethyl formamide was added (3.5 ml, 0.0275 mole) triethylamine and (3.4 g, 0.025 mole) 1-hydroxybenzotriazole followed by (5.3 g, 0.0275 mole) 1-ethyl-3-(3-dimethylaminopropyl)carbodiimide hydrochloride (ECDI). A slight exotherm was observed and the reaction mixture was allowed to stir at room temperature overnight. The reaction mixture was filtered and the filtrate concentrated in vacuo. The residue was extracted into ethyl acetate which was washed with water, dilute HCl, water, $NaHCO_3$ solution, water and then dried over magnesium sulfate. The magnesium sulfate was removed by filtration and the filtrate concentrated in vacuo yielding a solid residue 6 g (95%) of product which was recrystallizable from THF-ether, mp. 88°–89°; NMR (DMSO-d$_6$) δ 0.89 (d, 12); 1.12–1.95 (m, 6); 3.85 (m, 1); 4.27 (m, 1); 5.43 (d, 1); 6.92 (s, 1); 7.30 (s, 1); 7.52 (d, 1).

Anal: Calcd: for $C_{12}H_{24}N_2O_3$: C, 59.0; H, 9.9; N, 11.5. Found: C, 59.3; H, 10.6; N, 11.5.

EXAMPLE 3

Acetyl-L-Prolyl-L-Leucylglycyl-L-α-hydroxycaproyl-L-Leucine Amide

To a solution of (0.19 g, 0.0012 mole) carbonyldiimidazole in 5 ml methylene chloride was added (0.39 g, 0.0012 mole) acetyl-L-prolyl-L-Leucylglycine followed by (0.25 g, 0.001 mole) N-(L-α-hydroxyisocaproyl)-L-leucine amide dissolved in 5 ml methylene chloride. The reaction was stirred at room temperature for four days. It then was washed with water, dilute HCl, water, saturated NaHCO$_3$ and water and the organic phase was dried over magnesium sulfate. The magnesium sulfate was removed by filtration and the filtrate was concentrated in vacuo yielding a solid residue 0.3 g (55%), a sample of which was purified by the chromatographic method described below. The peptolide had a correct amino acid analysis, a mass molecular weight of 553 and a single HPLC peak.

Anal: Calcd. for $C_{27}H_{47}O_7N_5$: C, 58.6; H, 8.6; N, 12.6. Found: C, 58.5; H, 8.7; N, 12.5.

EXAMPLE 4

N-(L-α-Hydroxyisocaproyl)-L-alanine Amide

To a solution of (0.69 g, 5.5 mmole) L-alanine amide hydrochloride and (0.66 g, 5.0 mmole) L-α-hydroxyisocaproic acid in 25 ml dimethylformamide was added (0.77 ml, 5.5 mmole) triethylamine and (0.68 g, 5.0 mmole) 1-hydroxybenzotriazole followed by (1.06 g, 5.5 mmole) ECDI. A slight exotherm was observed and the solution stirred overnight at room temperature. The reaction mixture was filtered and the filtrate concentrated in vacuo. The residue was partitioned between ethylacetate and salt water (saturated) and the ethylacetate layer was dried over magnesium sulfate. The magnesium sulfate was removed by filtration and the filtrate concentrated in vacuo yielding a syrupy residue 0.77 g (76%) which slowly crystallized. The product was recrystallizable from methylene chloride and had a single peak in the HPLC, mass molecular weight of 202, NMR (DMSO d$_6$) δ 0.97 (d,6); 1.5–2.1 (m,3); 1.2 (d,3); 3.86 (m,1); 4.22 (t,1); 5.47 (d,1); 7.05 (s,1); 7.38 (s,1); 7.62 (d,1).

Anal: Calcd. for $C_9H_{18}N_2O_3$: C, 53.4; H, 9.0; N, 13.9, Found: C, 53.5; H, 9.2; N, 13.8.

EXAMPLE 5

Acetyl-L-Prolyl-L-Leucylglycyl-L-α-hydroxyisocaproyl-L-Alanine Amide

To a solution of (0.18 g, 1.1 mmole) carbonyldiimidazole in 5 ml methylene chloride was added (0.36 g, 1.1 mmole) acetyl-L-prolyl-L-leucylglycine followed by a solution of (0.203 g, 1.0 mmole) N-(L-α-hydroxyisocaproyl)-L-alanine amide in 5 ml methylene chloride. The resulting solution was stirred at room temperature overnight. The organic reaction solution was washed with salt water, dilute HCl in salt water, salt water, saturated NaHCO$_3$, salt water and dried over magnesium sulfate. The magnesium sulfate was removed by filtration and the filtrate concentrated in vacuo yielding a solid residue having a single peak in the HPLC, a mass molecular weight of 511 and a correct amino acid analysis.

Anal: Calcd. for $C_{24}H_{41}O_7N_5$: C, 54.4, H, 8.2. Found: C, 54.2; H, 8.3.

EXAMPLE 6

N-(L-α-Hydroxy-β-methylpentenoyl)-L-Leucine Amide

To a solution of (0.528 g, 4 mmole) L-isoleucic acid and (0.71 g, 4.4 mmole) L-leucine amide hydrochloride in 40 ml dimethyl formamide was added (0.61 ml, 4,4 mmole) triethylamine and (0.54 g, 4.0 mmole) 1-hydroxybenzotriazole followed by (0.84 g, 4.4 mmole) ECDI. The reaction mixture was stirred at room temperature overnight, then filtered and the filtrate concentrated in vacuo. The residue was partitioned between nearly saturated salt water and ethyl acetate and the organic phase was washed with dilute HCl, water, saturated NaHCO$_3$ and water (water nearly saturated with NaCl). The organic phase was dried over magnesium sulfate filtered to remove drying agent and concentrated in vacuo. The solid residue, 0.88 g (90%), showed a single peak in the HPLC and had an nmr consistent with the expected product. The product was used without further purification in the synthesis of the peptolide of Example 7.

EXAMPLE 7

Acetyl-L-Prolyl-L-Leucylglycyl-L-α-Hydroxy-β-methylpentanoyl-L-Leucine Amide

To a solution of (0.36 g, 2.2 mmole) carbonyldiimidazole and (0.72 g, 2.2 mmole) Acetyl-L-prolyl-L-leucylglycine in 20 ml methylene chloride allowed to stand at room temperature for 20 minutes was added (0.5 g, 2.0 mmole) N-(1-α-hydroxy-β-methylpentanoyl)-L-leucine amide and the solution then was stirred at room temperature for 40 hours. The solution was washed with water, dilute HCl, water, saturated NaHCO$_3$ and water (aqueous phase nearly saturated with NaCl). The washed organic phase was dried over magnesium sulfate, filtered to remove drying agent and concentrated in vacuo. The solid residue, 0.84 g (76%), appeared to be contaminated with starting product and a portion was purified by the chromatographic method described below, yielding peptolide with a single peak in the HPLC, a correct amino acid analysis, and a mass molecular weight of 553.

Anal: Calcd. for $C_{27}H_{47}O_7N_5.H_2O$: 5, 56.9; H, 8.7; N, 12.0. Found: C, 56.7; H, 8.6; N, 12.2.

The following example illustrates the chromatographic method used for purification of the peptides prepared in Example 1, above.

EXAMPLE 8

Chromatographic Method for Purification of Peptides

The crude peptide, after removal from resin by hydrogen fluoride, is extracted into water, neutralized to pH 6–7 and the water is then removed in vacuo. A portion of the residue is redissolved in a minimum of water and pipetted onto a 2 cm×15 cm C$_{18}$ reverse-phase chromatographic column. The column is washed with three column volumes of water using a Gilson peristaltic pump. A step gradient of methanol/water, acetonitrile/water or acetonitrile/water-pH 2.5 (trifluoroacetic acid) is passed through the column to selectively elute components. The eluted fractions are monitored by HPLC and fractions rich in the desired component are pooled and lyophilized.

The following Examples 9 and 10 illustrate the chromatographic assay (by HPLC) of collagenase cleavage of the peptides and peptolides prepared in the foregoing Examples 1 to 7. The collagenase used in these Examples was prepared from culture media of human skin fibroblasts according to the procedure of Stricklin et al., *Biochemistry*, 16, 1607 (1977).

EXAMPLE 9

Rate of Cleavage of Synthetic Substrates by Collagenase, HPLC Method

Substrate samples of 0.2–1.0 mg are weighed on a six-place balance, then dissolved in 0.05 M Tris buffer at pH 7.5 containing 0.01 M calcium chloride. The substrate concentration is adjusted to be $5.0 \times 10^{-4}$ M when all ingredients are combined. The collagenase, dissolved in the same media, is activated by trypsin (10 mg/ml in 0.001 M HCl) by adding one part trypsin solution to a hundred parts collagenase solution and allowing that solution to stand at room temperature for twenty minutes. The trypsin is inactivated by adding twenty parts soybean trypsin inhibitor (5 mg/ml in 0.05 M Tris with 0.01 M $CaCl_2$).

The activated collagenase is added to the substrate solution, stirred, and a sample injected into the HPLC as a zero time measurement. The remaining sample is kept in a 35° bath and additional aliquots are removed and assayed at appropriate time intervals. The cleavage rate is determined by measuring the appearance of the peak assigned to cleavage product and/or the disappearance of the peak assigned to starting product.

EXAMPLE 10

Applying the HPLC procedure of Example 9, the novel peptides and peptolides of the present invention (Samples A, B, C, D, E) exhibited the following relative rates of activity in comparison to the rates of activity of the commercially available synthetic collagenase substrates (Samples F and G):

| Sample No. | Product | Relative Rate |
| --- | --- | --- |
| A | Ac—Pro—Leu—Gly—Ile—Leu—Gly—Leu—OH | 100 |
| B | Ac—Gly—Pro—Leu—Gly—Ile—Leu—Gly—Ala—OH | 80 |
| C | Ac—Pro—Leu—Gly—(O—Leu)—Leu—$NH_2$ | 80 |
| D | Ac—Pro—Leu—Gly—(O—Ile)—Leu—$NH_2$ | 75 |
| E | Ac—Pro—Leu—Gly—(O—Leu)—Ala—$NH_2$ | 65 |
| F | DNP—Pro—Leu—Gly—Ile—Ala—Gly—Arg—$NH_2$ | 10 |
| G | DNP—Pro—Gln—Gly—Ile—Ala—Gly—Gln—D-Arg—OH | 2 |

Various other examples will be apparent to the person skilled in the art after reading the present disclosure without departing from the spirit and scope of the invention and it is intended that all such further examples be included within the scope of the appended claims. For example, the terminal carboxyl groups in the foregoing peptides and peptolides can readily be converted to ester groups such as ethyl, benzyl, p-nitrobenzyl or t-butyl ester groups, and other N-protecting groups such as t-BOC and carbobenzoxy can readily be used in place of the acetyl groups or the N-protecting group can readily be removed without departing from the basic and novel properties of the invention.

What is claimed is:

1. A method for the determination of collagenase in a biological sample comprising reacting an aqueous solution of said sample with a peptide or peptolide substrate selected from the group consisting of $R_1$-Pro-Leu-Gly-Ile-Leu-Gly-Leu-$R_2$,
$R_1$-Gly-Pro-Leu-Gly-Ile-Leu-Gly-Ala-$R_2$,
$R_1$-Pro-Leu-Gly(O-Ile)-Leu-$R_2$,
$R_1$-Pro-Leu-Gly(O-Leu)-$R_2$, and
$R_1$-Pro-Leu-Gly(O-Leu)-Ala-$R_2$,
wherein
$R_1$ is H or N-protecting group, and
$R_2$ is terminal amide, carboxyl or ester group, under conditions suitable for the enzymatic cleavage of the substrate to form a product, and measuring the amount of product formed or unreacted substrate.

2. The method of claim 1 in which the substrate is a peptide selected from the group consisting of
Ac-Pro-Leu-Gly-Ile-Leu-Gly-Leu-OH, and
Ac-Gly-Pro-Leu-Gly-Ile-Leu-Gly-Ala-OH.

3. The method of claim 1 in which the substrate is a peptolide selected from the group consisting of
Ac-Pro-Leu-Gly(O-Ile)-Leu-$NH_2$,
Ac-Pro-Leu-Gly(O-Leu)-Leu-$NH_2$, and
Ac-Pro-Leu-Gly(O-Leu)-Ala-$NH_2$.

* * * * *

UNITED STATES PATENT AND TRADEMARK OFFICE
CERTIFICATE OF CORRECTION

PATENT NO. : 4,425,428
DATED : January 10, 1984
INVENTOR(S) : HAROLD I. WEINGARTEN It is certified that error appears in the above—identified patent and that said Letters Patent is hereby corrected as shown below:

In Col. 10, line 35, the fourth listed peptide of

Claim 1 should read:

"$R_1$-Pro-Leu-Gly(0-Leu)-Leu-$R_2$".

Signed and Sealed this

Fifteenth Day of January 1985

[SEAL]

Attest:

Attesting Officer

GERALD J. MOSSINGHOFF

*Commissioner of Patents and Trademarks*